United States Patent [19] [11] 4,187,224
Axen [45] Feb. 5, 1980

[54] 2-DECARBOXY-2-HYDROXYMETHYL-5,6-DIHYDRO-PROSLACYLIN ANALOGS

[75] Inventor: Udo F. Axen, Plainwell, Mich.

[73] Assignee: The Upjohn Company, Kalamazoo, Mich.

[21] Appl. No.: 916,634

[22] Filed: Jun. 19, 1978

Related U.S. Application Data

[60] Division of Ser. No. 857,236, Dec. 5, 1977, Pat. No. 4,125,712, which is a continuation-in-part of Ser. No. 788,146, Apr. 19, 1977, abandoned, which is a continuation-in-part of Ser. No. 691,400, Jun. 1, 1976, abandoned.

[51] Int. Cl.² ........................................... C07D 307/93
[52] U.S. Cl. .............................. 260/346.22; 542/426; 542/429
[58] Field of Search .................. 260/346.22; 542/426, 542/429

[56] References Cited
PUBLICATIONS
Johnson et al., Prostaglandins, vol. 12, p. 915 (1976).

Primary Examiner—Alan L. Rotman
Assistant Examiner—Bernard Dentz
Attorney, Agent, or Firm—Morris L. Nielsen

[57] ABSTRACT

2-Decarboxy-2-hydroxymethyl-5,6-dihydro-prostacyclin analogs ($PGI_1$ derivatives) illustrated by a compound of the formula

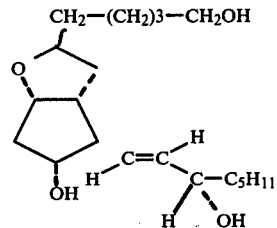

wherein ~ indicates alpha or beta configuration, and the processes for producing them, said analogs having pharmacological utility.

28 Claims, No Drawings

2-DECARBOXY-2-HYDROXYMETHYL-5,6-DIHYDRO-PROSLACYLIN ANALOGS

CROSS REFERENCE TO RELATED APPLICATIONS

This application is a divisional of copending application Ser. No. 857,236 filed Dec. 5, 1977 now issued as U.S. Pat. No. 4,125,712, which was a continuation-in-part of then copending Ser. No. 788,146 filed Apr. 19, 1977, since abandoned, which was a continuation-in-part of then copending Ser. No. 691,400 filed June 1, 1976, since abandoned.

BACKGROUND OF THE INVENTION

This invention relates to products having prostacyclin-like structure and to processes for preparing them. In particular this invention relates to 2-decarboxy-2-hydroxymethyl 5,6-dihydro-prostacyclin analogs and to processes for preparing them.

The essential material for this application, including the background of the invention, the disclosure of the invention, and the description of the preferred embodiments, including Preparations and Examples, is incorporated by reference from commonly owned U.S. Pat. No. 4,125,712, under the provision of M.P.E.P. 608.01(p).

SUMMARY OF THE INVENTION

It is the purpose of this invention to provide novel products having pharmacological activity. It is a further purpose to provide processes for preparing these products and their intermediates.

The terms L, $Q_2$, etc. as used hereinafter are as defined in the Table of Definitions herein.

TABLE

Definition of Terms for Formulas

A is
  a valence bond or —$(CH_2)_h$— where h is one, 2, or 3.
D is
  (1) a valence bond; (2) —$(CH_2)_d$— where d is one, 2, 3, 4, or 5; (3) —CH=CH—A— where A is a valence bond or —$(CH_2)_h$— where h is one, 2, or 3; or (4) —$CH_2$—O—$CH_2$—Y— where Y is a valence bond or —$(CH_2)_k$— where k is one or 2.
D' is
  —$CH_2$—CH=CH—A— or —$(CH_2)_t$—$CF_2$— wherein A is a valence bond or —$(CH_2)_h$— where h is one, 2, or 3; and wherein t is 2, 3, or 4.
E is
  alkyl of one to 4 carbon atoms, inclusive, phenyl, phenyl substituted with one to 2 fluoro, chloro, or alkyl of one to 4 carbon atoms, inclusive, or aralkyl of 7 to 12 carbon atoms, inclusive.
G is
  nitrato, iodo, chloro, bromo, acetato, trifluoroacetato, or benzoato.
L is
  (1) a valence bond, (2) —$(CH_2)_d$— wherein d is one to 5 inclusive, (3) —$(CH_2)_t$—$CF_2$— wherein t is 2, 3, or 4, (4) —$CH_2$—CH=CH—A— wherein A is a valence bond or —$(CH_2)_h$— wherein h is one, 2, or 3, or (5) —$CH_2$—O—$CH_2$—Y— wherein Y is a valence bond or —$(CH_2)_k$— wherein k is one or 2.
$L_1$ is

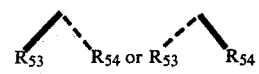

or a mixture of

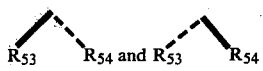

wherein $R_{53}$ and $R_{54}$ are hydrogen, methyl, or fluoro, being the same or different, with the proviso that one of $R_{53}$ and $R_{54}$ is fluoro only when the other is hydrogen or fluoro.

$L_2$ and $L_3$ are
  hydrogen, alkyl of one to 4 carbon atoms, inclusive, or —$COOR_{51}$, wherein $R_{51}$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted one, 2, or 3 chloro or alkyl of one to 3 carbon atoms, inclusive; being the same or different, with the proviso that not more than one of $L_2$ and $L_3$ is —$COOR_{51}$.

M is
  —$(CH_2)_h$ wherein h is one, 2, or 3.

$M_1$ is

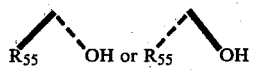

wherein $R_{55}$ is hydrogen or methyl.

Q is

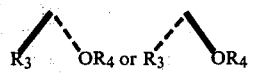

wherein $R_3$ is hydrogen or alkyl of one to 4 carbon atoms, inclusive, and wherein $R_4$ is hydrogen, tetrahydropyran-2-yl, tetrahydrofuranyl, 1-ethoxyethyl or a group of the formula

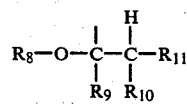

wherein $R_8$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_9$ and $R_{10}$ are the same or different, being hydrogen, alkyl of one to 4 carbon atoms, inclusive, phenyl or phenyl substituted with one, 2, or 3 alkyl of one to 4 carbon atoms, inclusive, or, when $R_9$ and $R_{10}$ are taken together, —$(CH_2)_a$— or —$(CH_2)_b$—O—$(CH_2)_c$— wherein "a" is 3, 4, or 5, b is one, 2, or 3, and c is one, 2, or 3 with the proviso that b plus c is 2, 3, or 4, and wherein $R_{11}$ is hydrogen or phenyl.

$Q_1$ is

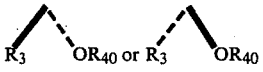

wherein $R_3$ is as defined above, and wherein $R_{40}$ is the same as $R_4$ defined above except that it does not include hydrogen, but includes only the blocking groups such as tetrahydropyran-2-yl.

$Q_2$ is

wherein $R_3$ and $R_4$ are as defined above for Q.

$Q_3$ is

wherein $R_3$ is hydrogen or alkyl of one to 4 carbon atoms, inclusive.

$Q_4$ is

$Q_5$ is

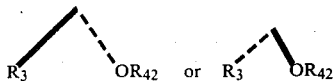

wherein $R_{42}$ is (1) tetrahydropyran-2-yl, (2) tetrahydrofuranyl, (3) 1-ethoxyethyl, (4) a group of the formula

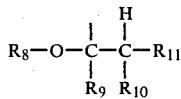

wherein $R_8$ is alkyl of one to 18 carbon atoms, inclusive, cycloalkyl of 3 to 10 carbon atoms, inclusive, phenyl, or phenyl substituted with one, 2, or 3 alkyl of one to 4 carbon atoms, inclusive, wherein $R_9$ and $R_{10}$ are the same or different, being hydrogen, alkyl of one to 4 carbon atoms, inclusive, phenyl or phenyl substituted with one, 2, or 3 alkyl of one to 4 carbon atoms, inclusive, or, when $R_9$ and $R_{10}$ are taken together, —(CH$_2$)$_a$— or —(CH$_2$)$_b$—O—(CH$_2$)$_c$— wherein a is 3, 4, or 5, b is one, 2, or 3, and c is one, 2, or 3 with the proviso that b plus c is 2, 3, or 4, and wherein $R_{11}$ is hydrogen or phenyl, or (5) a silyl group of the formula —Si(E)$_3$ wherein E is alkyl of one to 4 carbon atoms, inclusive, phenyl, phenyl substituted with one or 2 fluoro, chloro, or alkyl of one to 4 carbon atoms, inclusive, or aralkyl of 7 to 12 carbon atoms, inclusive.

$Q_6$ is

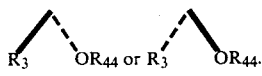

wherein $R_{44}$ is $R_{42}$ as defined for $Q_5$ and hydrogen.

$R_1$ is
hydrogen or alkyl of one to 8 carbon atoms, inclusive, or a pharmacologically acceptable cation.

$R_2$ is

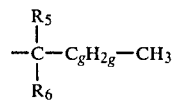

wherein $C_gH_{2g}$ is alkylene of one to 9 carbon atoms, inclusive, with one to 5 carbon atoms, inclusive, in the chain between —CR$_5$R$_6$— and terminal methyl, wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro; or

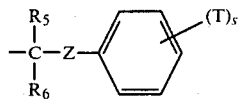

wherein $R_5$ and $R_6$ are as defined above with the proviso that neither $R_5$ nor $R_6$ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between —CR$_5$R$_6$—and the phenyl ring; wherein T is alkyl of one to 4 carbon atoms, inclusive, fluoro, chloro, trifluoromethyl, or —OR$_7$— wherein $R_7$ is alkyl of one to 4 carbon atoms, inclusive, and s is zero, one, 2, or 3, with the proviso that not more than two T's are other than alkyl and when s is 2 or 3 the T's are either the same or different.

$R_3$ is
hydrogen or alkyl of one to 4 carbon atoms.

$R_4$ is
hydrogen, tetrahydropyran-2-yl, tetrahydrofuranyl, 1-ethoxyethyl or a group of the formula

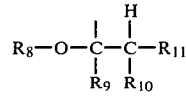

wherein $R_8$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_9$ and $R_{10}$ are the same or different, being hydrogen, alkyl of one to 4 carbon atoms, inclusive, phenyl or phenyl substituted with one, 2, or 3 alkyl of one to 4 carbon atoms, inclusive, or, when $R_9$ and $R_{10}$ are taken together, —(CH$_2$)$_a$— or —(CH$_2$)$_b$—O—(CH$_2$)$_c$— wherein "a" is 3, 4, or 5, b is one, 2, or 3, and c is one, 2, or 3 with the proviso that b plus c is 2, 3, or 4, and wherein $R_{11}$ is hydrogen or phenyl.

$R_5$ and $R_6$ are
hydrogen, alkyl of one to 4 carbon atoms, inclusive, or fluoro, being the same or different, with the proviso that one of $R_5$ and $R_6$ is fluoro only when the other is hydrogen or fluoro, and with the further proviso that, when Z is oxa (—O—) as defined below, neither $R_5$ nor $R_6$ is fluoro.

$R_7$ is
alkyl of one to 4 carbon atoms, inclusive.

$R_8$ is
alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive.

$R_9$ and $R_{10}$ are
the same or different, being hydrogen, alkyl of one to 4 carbon atoms, inclusive, phenyl or phenyl substituted with one, 2, or 3 alkyl of one to 4 carbon atoms, inclusive, or, when $R_9$ and $R_{10}$ are taken together, —(CH$_2$)$_a$— or —(CH$_2$)$_b$—O—(CH$_2$)$_c$— wherein a is 3, 4, or 5, b is one, 2, or 3, and c is one, 2, or 3 with the proviso that b plus c is 2, 3, or 4.

$R_{11}$ is
  hydrogen or phenyl.
$R_{12}$ is
  alkyl of one to 8 carbon atoms, inclusive.
$R_{13}$ is
  the group $-P^+(C_6H_5)_3$ or $-P(O)(OR_{12})_2$ wherein $R_{12}$ is as defined above.
$R_{14}$ is
  hydrogen or an alkali metal cation.
$R_{15}$ is
  alkyl of one to 3 carbon atoms, inclusive.
$R_{16}$ is
  (1) $-COOR_{17}$
  (2) $-CH_2OH$
  (3) $-CH_2N(R_{18})_2$

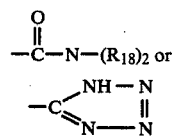

wherein $R_{17}$ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl with one, 2, or 3 chloro or alkyl of one to 4 carbon atoms, inclusive, or (g) 2-naphthyl; and wherein $R_{18}$ is hydrogen, alkyl of one to 12 carbon atoms, inclusive, benzyl, or phenyl, being the same or different.

$R_{17}$ is
  as defined in $R_{16}$ above.
$R_{18}$ is
  as defined in $R_{16}$ above.
$R_{19}$ is
  (a) alkyl of one to 12 carbon atoms, inclusive,
  (b) cycloalkyl of 3 to 10 carbon atoms, inclusive,
  (c) aralkyl of 7 to 12 carbon atoms, inclusive,
  (d) phenyl,
  (e) phenyl substituted with one, 2, or 3 chloro or alkyl of one to 4 carbon atoms, inclusive,

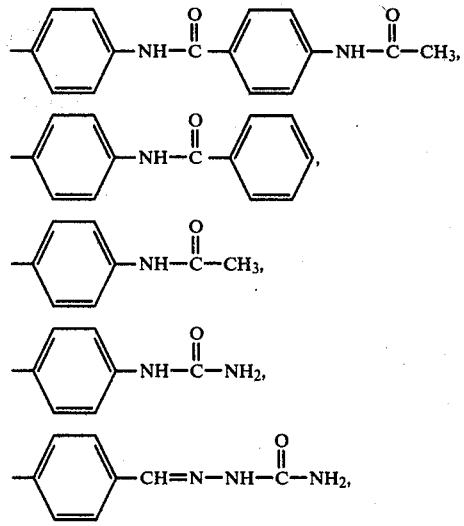

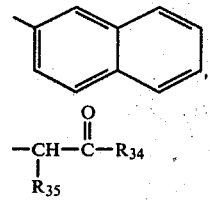

wherein $R_{34}$ is phenyl, p-bromophenyl, p-biphenylyl, p-nitrophenyl, p-benzamidophenyl, or 2-naphthyl, and wherein $R_{35}$ is hydrogen or benzoyl,
  (m) hydrogen; or
  (n) a pharmacologically acceptable cation $R_{20}$ is

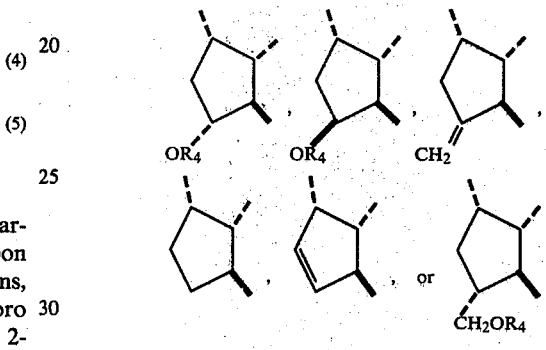

wherein $R_4$ is as defined above. $R_{21}$ is the same as $R_{20}$ defined above except that $R_4$ therein is replaced with $R_{40}$ as defined below, i.e. excluding hydrogen. $R_{22}$ is

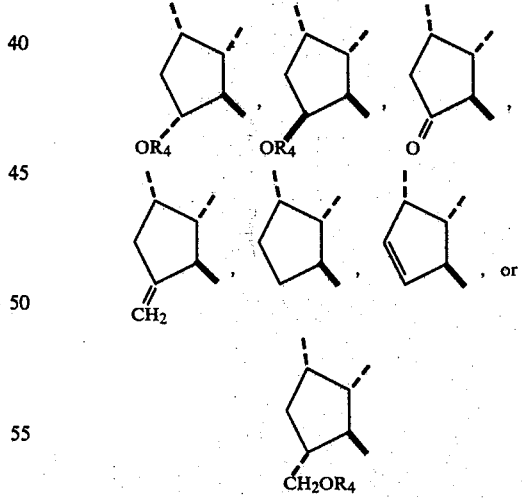

wherein $R_4$ is as defined above.
$R_{25}$ includes
  $R_2$, as defined above, and

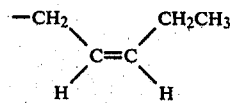

$R_{23}$ is

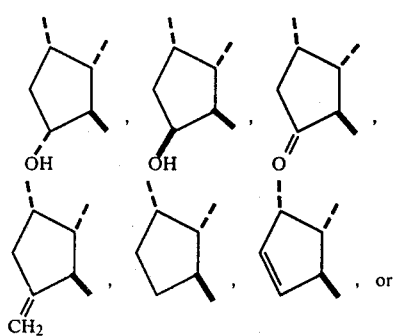

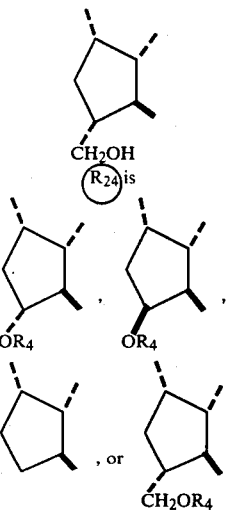

$R_{26}$ is
a carboxyacyl blocking group:

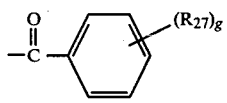
(1)

wherein $R_{27}$ is alkyl of one to 4 carbon atoms, inclusive, phenylalkyl of 7 to 10 carbon atoms, inclusive, phenyl or nitro, and g is zero to 5, inclusive, provided that not more than two $R_{27}$'s are other than alkyl, and that the total number of carbon atoms in the $R_{27}$'s does not exceed 10 carbon atoms:

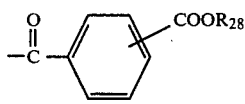
(2)

wherein $R_{28}$ is alkyl of one to 4 carbon atoms, inclusive; or

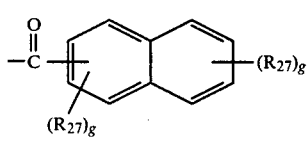
(3)

wherein $R_{27}$ and g are as defined above.
$R_{27}$ is
as defined in $R_{26}$ above.

$R_{28}$ is
as defined in $R_{26}$ above.

$R_{30}$ is
(1) —COOR$_{19}$
(2) —CH$_2$OH
(3) —CH$_2$N(R$_{18}$)$_2$

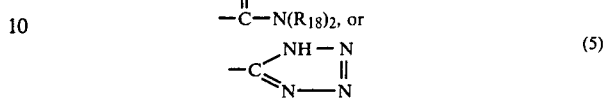
(4)

(5)

wherein $R_{19}$ is
(a) alkyl of one to 12 carbon atoms, inclusive,
(b) cycloalkyl of 3 to 10 carbon atoms, inclusive,
(c) aralkyl of 7 to 12 carbon atoms, inclusive,
(d) phenyl,
(e) phenyl substituted with one, 2, or 3 chloro or alkyl of one to 4 carbon atoms, inclusive,

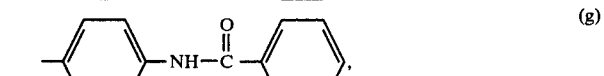
(f)

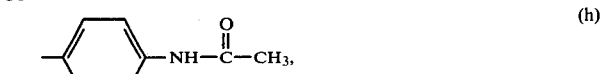
(g)

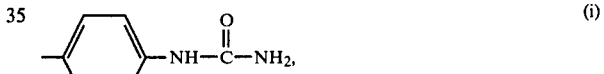
(h)

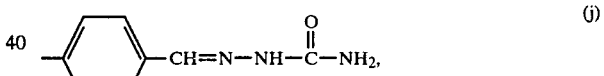
(i)

(j)

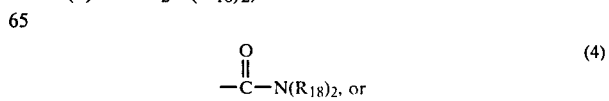
(k)

—CH—C—R$_{34}$
    |          ||
    R$_{35}$   O
(l)

wherein $R_{34}$ is phenyl, p-bromophenyl, p-biphenylyl, p-nitrophenyl, p-benzamidophenyl, or 2-naphthyl, and wherein $R_{35}$ is hydrogen or benzoyl,
(m) hydrogen; or
(n) a pharmacologically acceptable cation; and wherein $R_{18}$ is hydrogen, alkyl of one to 12 carbon atoms, inclusive, benzyl, or phenyl, being the same or different.

$R_{31}$ is
(1) —COOR$_{32}$
(2) —CH$_2$OH, with the proviso that $R_{31}$ is not —CH$_2$OH when D is a valence bond,
(3) —CH$_2$N(R$_{18}$)$_2$, —C—N(R$_{18}$)$_2$, or
‖
O
(4)

$$-C\begin{array}{c}NH-N\\ \parallel\\ N-N\end{array}\quad (5)$$

wherein R$_{32}$ is
(a) cycloalkyl of 3 to 10 carbon atoms, inclusive,
(b) aralkyl of 7 to 12 carbon atoms, inclusive,
(c) phenyl,
(d) phenyl substituted with one, 2, or 3 chloro or alkyl of one to 4 carbon atoms, inclusive, (e) —C$_6$H$_4$—NH—CO—C$_6$H$_4$—NH—CO—CH$_3$, (f) —C$_6$H$_4$—NH—CO—C$_6$H$_5$, (g) —C$_6$H$_4$—NH—CO—CH$_3$, (h) —C$_6$H$_4$—NH—CO—NH$_2$, (i) —C$_6$H$_4$—CH=N—NH—CO—NH$_2$, (j) 2-naphthyl, or (k) —CH(R$_{35}$)—CO—R$_{34}$ wherein R$_{34}$ is phenyl, p-bromophenyl, p-biphenylyl, p-nitrophenyl, p-benzamidophenyl, or 2-naphthyl, wherein R$_{35}$ is hydrogen or benzoyl, and wherein R$_{18}$ is hydrogen, alkyl of one to 12 carbon atoms, inclusive, benzyl, or phenyl, being the same or different; wherein ~ indicates attachment in alpha or beta configuration; including the lower alkanoates thereof.

R$_{32}$ is
  as defined in R$_{31}$ above.
R$_{33}$ is
  iodo or bromo.
R$_{34}$ is
  phenyl, p-bromophenyl, p-biphenylyl, p-nitrophenyl, p-benzamidophenyl, or 2-naphthyl.
R$_{35}$ is
  hydrogen or benzoyl.
R$_{36}$ is
  (1) —COOR$_{37}$
  (2) —CH$_2$OH
  (3) —CH$_2$N(R$_{18}$)$_2$ (4) —CO—N(R$_{18}$)$_2$, or $$-C\begin{array}{c}NH-N\\ \parallel\\ N-N\end{array}\quad (5)$$

wherein R$_{37}$ is
(a) alkyl of one to 12 carbon atoms, inclusive,
(b) cycloalkyl of 3 to 10 carbon atoms, inclusive,
(c) aralkyl of 7 to 12 carbon atoms, inclusive,
(d) phenyl,
(e) phenyl substituted with one, 2, or 3 chloro or alkyl of one to 4 carbon atoms, inclusive, (f) —C$_6$H$_4$—NH—CO—C$_6$H$_4$—NH—CO—CH$_3$, (g) —C$_6$H$_4$—NH—CO—C$_6$H$_5$, (h) —C$_6$H$_4$—NH—CO—CH$_3$, (i) —C$_6$H$_4$—NH—CO—NH$_2$, (j) —C$_6$H$_4$—CH=N—NH—CO—NH$_2$, (k) 2-naphthyl, (l) —CH(R$_{35}$)—CO—R$_{34}$ wherein R$_{34}$ is phenyl, p-bromophenyl, p-biphenylyl, p-nitrophenyl, p-benzamidophenyl, or 2-naphthyl, and wherein R$_{35}$ is hydrogen or benzoyl, or
  (m) hydrogen; and wherein R$_{18}$ is hydrogen, alkyl of one to 12 carbon atoms, inclusive, benzyl, or phenyl, being the same or different.

R$_{37}$ is
  as defined above in R$_{36}$.
R$_{38}$ is
  bromo or chloro.
R$_{40}$ is
  the same as R$_4$ defined above except that it does not include hydrogen, but only the blocking groups such as tetrahydropyran-2-yl. R$_{41}$ is

[three cyclopentane structures: two with OR$_{42}$ substituents and one with =CH$_2$]

-continued

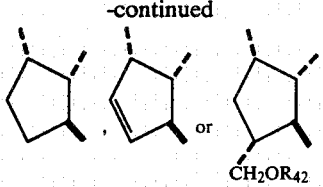

wherein R$_{42}$ includes R$_{40}$ blocking groups as defined above, together with silyl groups of the formula -Si(E)$_3$ wherein E is alkyl of one to 4 carbon atoms, inclusive, phenyl, phenyl substituted with one or 2 fluoro, chloro, or alkyl of one to 4 carbon atoms, inclusive, or aralkyl of 7 to 12 carbon atoms, inclusive.

R$_{42}$ is
as defined in (R$_{41}$). (R$_{43}$) is

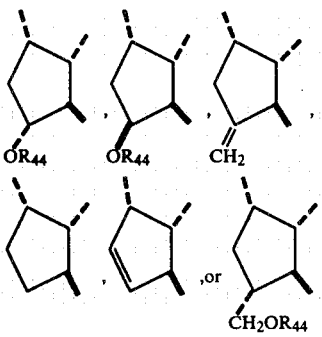

wherein R$_{44}$ includes R$_{42}$ blocking groups and hydrogen.

R$_{44}$ is
is as defined in (R$_{43}$).

R$_{51}$ is
hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted one, 2, or 3 chloro or alkyl of one to 3 carbon atoms, inclusive.

R$_{53}$ and R$_{54}$ are
hydrogen, methyl, or fluoro, being the same or different, with the proviso that one of R$_{53}$ and R$_{54}$ is fluoro only when the other is hydrogen or fluoro.

R$_{55}$ is
hydrogen or methyl.

R$_{57}$ is
(1) —(CH$_2$)$_m$—CH$_3$—,

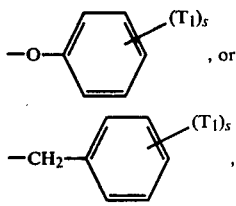

wherein m is one to 5, inclusive, T$_1$ is chloro, fluoro, trifluoromethyl, alkyl of one to 3 carbon atoms, inclusive, or alkoxy of one to 3 carbon atoms, inclusive, and s is zero, one, 2, or 3, the various T$_1$'s being the same or different, with the proviso that not more than two T$_1$'s are other than alkyl.

R$_{58}$ is
hydrogen or hydroxy.

T is
alkyl of one to 4 carbon atoms, inclusive, fluoro, chloro, trifluoromethyl, or —OR$_7$— wherein R$_7$ is hydrogen or alkyl of one to 4 carbon atoms, inclusive, and s is zero, one, 2, or 3, with the proviso that not more than two T's are other than alkyl and when s is 2 or 3 the T's are either the same or different.

T$_1$ is
chloro, fluoro, trifluoromethyl, alkyl of one to 3 carbon atoms, inclusive, or alkoxy of one to 3 carbon atoms, inclusive, and s is zero, one, 2, or 3, the various T$_1$'s being the same or different, with the proviso that not more than two T$_1$'s are other than alkyl.

W is

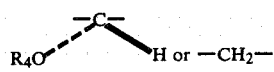

wherein R$_4$ is as defined above.

X is
trans—CH=CH—, cis—CH=CH—, —C≡C—, or —CH$_2$CH$_2$—.

X' is
cis—CH=CH—, —C≡C—, or —CH$_2$CH$_2$—.

Y is
a valence bond or —(CH$_2$)$_k$— where k is one or 2.

Y$_1$ is
trans—CH=CH—; —C≡C— or —CH$_2$CH$_2$—.

Z is
an oxa atom (—O—) or C$_j$H$_{2j}$ is a valence bond or alkylene of one to 9 carbon atoms, inclusive, substituted with zero, one, or 2 fluoro, with one to 6 carbon atoms, inclusive between —CR$_5$R$_6$— and the phenyl ring.

Z$_1$ is
(1) cis—CH=CH—CH$_2$—(CH$_2$)$_g$—CH$_2$—, or
(2) cis—CH=CH—CH$_2$—(CH$_2$)$_g$—CF$_2$—,
wherein g is one, 2, or 3.

a is
3, 4, or 5.

b is
one, 2, or 3.

c is
one, 2, or 3 with the proviso that b plus c is 2, 3, or 4.

d is
an integer of one to 5, inclusive.

g (as to (R$_{27}$)$_g$ in carboxyacyl groups) is zero to 5, inclusive.

g (as to —(CH$_2$)$_g$— in Z$_1$ of Preparation 1) is one, 2, or 3.

h is
one, 2 or 3.

k is
one or 2.

m is
one to 5, inclusive.

s is
zero, one, 2, or 3.

t is
2, 3, or 4.

Hal is
chloro, bromo, or iodo.

THP is
tetrahydropyran-2-yl.

Ts is
  p-toluenesulfonyl.
The symbol ~ (wavy line) indicates
  attachment in alpha or beta configuration.
$C_gH_{2g}$ is
  alkylene of one to 9 carbon atoms, inclusive, with one to 5 carbon atoms, inclusive, in the chain between —$CR_5R_6$— and terminal methyl.
$C_jH_{2j}$ is
  a valence bond or alkylene of one to 9 carbon atoms, inclusive, substituted with zero, one, or 2 fluoro, with one to 6 carbon atoms, inclusive between —$CR_5R_6$— and the phenyl ring.
Merely illustrative but not limiting are compounds of the following formula:

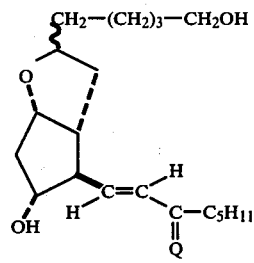

XXVI

I claim:
1. A cyclic ether of the formula

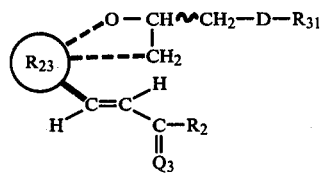

wherein D is (1) a valence bond; (2) —$(CH_2)_d$— where d is one, 2, 3, 4, or 5; (3) —CH=CH—A— where A is a valence bond or —$(CH_2)_h$— where h is one, 2, or 3; or (4) —$CH_2$—O—$CH_2$—Y— where Y is a valence bond or —$(CH_2)_k$— where k is one or 2; wherein $R_2$ is

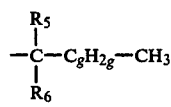    (1)

wherein $C_gH_{2g}$ is alkylene of one to 9 carbon atoms, inclusive, with one to 5 carbon atoms, inclusive, in the chain between —$CR_5R_6$— and terminal methyl, wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro; or

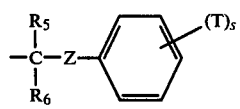   (2)

wherein $R_5$ and $R_6$ are as defined above with the proviso that neither $R_5$ nor $R_6$ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between —$CR_5R_6$— and the phenyl ring; wherein T is alkyl of one to 4 carbon atoms, inclusive, fluoro, chloro, trifluoromethyl, or —$OR_7$ wherein $R_7$ is alkyl of one to 4 carbon atoms, inclusive, and s is zero, one, 2, or 3, with the proviso that not more than two T's are other than alkyl and when s is 2 or 3 the T's are either the same or different;
wherein $Q_3$ is

wherein $R_3$ is hydrogen or alkyl of one to 4 carbon atoms, inclusive;
wherein $R_{23}$ is

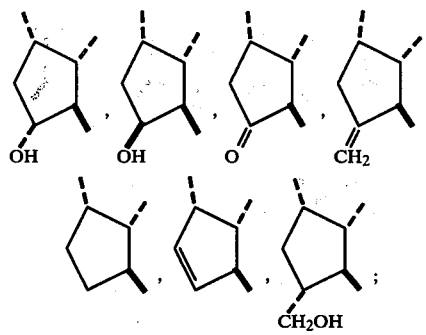

wherein $R_{31}$ is —$CH_2OH$ with the proviso that $R_{31}$ is not —$CH_2OH$ when D is a valence band,
and wherein ~ indicates attachment in alpha or beta configuration; including the lower alkanoates thereof.
2. A compound according to claim 1 wherein $Q_3$ is

wherein $R_3$ is as defined in claim 1.
3. A compound according to claim 2 wherein $R_3$ is hydrogen and $R_{23}$ is

4. A compound according to claim 3 wherein D is a valence bond or —$(CH_2)_d$— wherein d is one, 2, 3, 4, or 5.
5. A compound according to claim 4 wherein D is trimethylene.
6. A compound according to claim 5 wherein $R_2$ is n-pentyl.
7. A cyclic ether of the formula

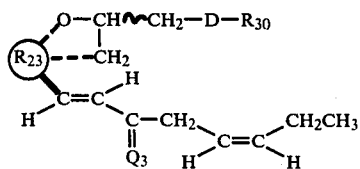

wherein D is (1) a valence bond; (2) —(CH$_2$)$_d$— where d is one, 2, 3, 4, or 5; (3) —CH═CH—A— where A is a valence bond, or —(CH$_2$)$_h$— where h is one, 2, or 3; or (4) —CH$_2$—O—CH$_2$—Y— where Y is a valence bond or —(CH$_2$)$_k$— where k is one or 2;
wherein Q$_3$ is

wherein R$_3$ is hydrogen or alkyl of one to 4 carbon atoms, inclusive;
wherein  is

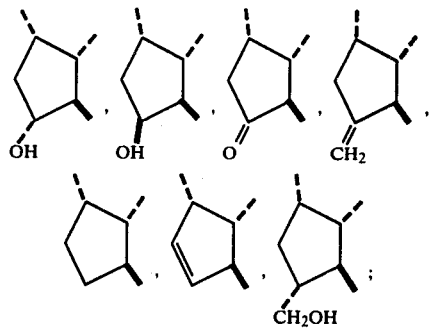

wherein R$_{30}$ is
—CH$_2$OH
and wherein ∼ indicates attachment in alpha or beta configuration; including the lower alkanoates thereof.

8. A compound according to claim 7 wherein Q$_3$ is

wherein R$_3$ is as defined in claim 29.

9. A compound according to claim 8 wherein (R$_{23}$) is

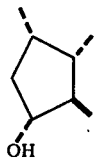

10. A compound according to claim 9 wherein D is a valence bond or —(CH$_2$)$_d$— wherein d is one, 2, 3, 4, or 5.

11. A cyclic ether of the formula

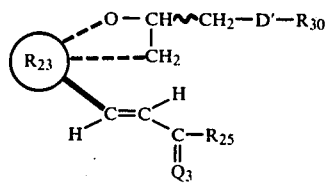

wherein D' is
—CH$_2$—CH═CH—A— or
—(CH$_2$)$_r$—CF$_2$—
wherein A is a valence bond or —(CH$_2$)$_h$— where h is one, 2, or 3; and wherein t is 2, 3, or 4;
wherein Q$_3$ is

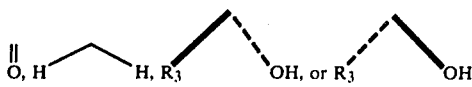

wherein R$_3$ is hydrogen or alkyl of one to 4 carbon atoms, inclusive,
wherein 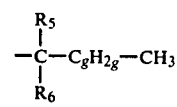 is

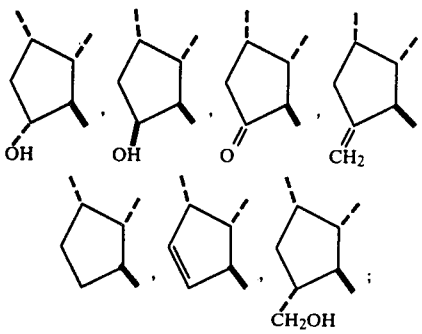

wherein R$_{25}$ is

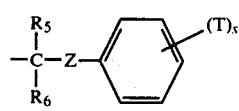 (1)

wherein C$_g$H$_{2g}$ is alkylene of one to 9 carbon atoms, inclusive, with one to 5 carbon atoms, inclusive, in the chain between —CR$_5$R$_6$— and terminal methyl, wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro;

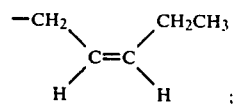 (2)

wherein R$_5$ and R$_6$ are as defined above with the proviso that neither R$_5$ nor R$_6$ is fluoro when Z is oxa (—O—); wherein Z represents an oxa atom (—O—) or C$_j$H$_{2j}$ wherein C$_j$H$_{2j}$ is a valence bond or alkylene of one to 9 carbon atoms, inclusive, with one to 6 carbon atoms, inclusive between —CR$_5$R$_6$— and the phenyl ring; wherein T is alkyl of one to 4 carbon atoms, inclusive, fluoro, chloro, trifluoromethyl, or —OR$_7$— wherein R$_7$ is alkyl of one to 4 carbon atoms, inclusive, and s is zero, one, 2, or 3, with the proviso that not more than two T's are other than alkyl and when s is 2 or 3 the T's are either the same or different; or

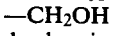 (3)

wherein R$_{30}$ is
—CH$_2$OH
and wherein ∼ indicates attachment in alpha or beta configuration; including the lower alkanoates thereof.

12. A compound according to claim 11 wherein $Q_3$ is

wherein $R_3$ is as defined in claim 35.

13. A compound according to claim 12 wherein $\text{\textcircled{R}}_{23}$ is

14. A compound according to claim 13 wherein D' is $-(CH_2)_t-CF_2$ where t is 2, 3, or 4.

15. A compound according to claim 13 wherein D' is $-CH_2CH=CH-A-$ wherein A is a valence bond or $-(CH_2)_h$ wherein h is one, 2, or 3.

16. A cyclic ether of the formula

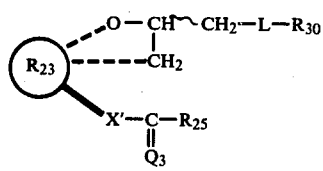

wherein L is (1) a valence bond, (2) $-(CH_2)_d-$ wherein d is one to 5 inclusive, (3) $-(CH_2)_t-CF_2-$ wherein t is 2, 3, or 4, (4) $-CH_2-CH=CH-A-$ wherein A is a valence bond or $-(CH_2)_h-$ wherein h is one, 2, or 3, or (5) $-CH_2-O-CH_2-Y-$ wherein Y is a valence bond or $-(CH_2)_k-$ wherein k is one or 2; wherein $Q_3$ is

wherein $R_3$ is hydrogen or alkyl of one to 4 carbon atoms, inclusive;
wherein $\text{\textcircled{R}}_{23}$ is

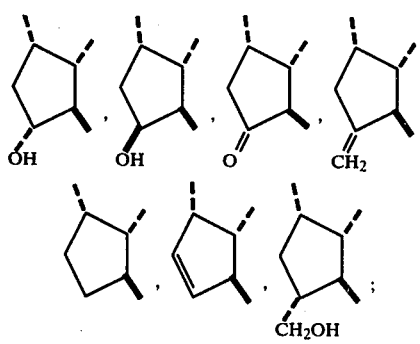

wherein $R_{25}$ is

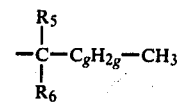  (1)

wherein $C_gH_{2g}$ is alkylene of one to 9 carbon atoms, inclusive, with one to 5 carbon atoms, inclusive, in the chain between $-CR_5R_6-$ and terminal methyl, wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro;

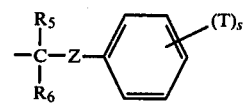  (2)

wherein $R_5$ and $R_6$ are as defined above with the proviso that neither $R_5$ nor $R_6$ is fluoro when Z is oxa ($-O-$); wherein Z represents an oxa atom ($-O-$) or $C_jH_{2j}$ wherein $C_jH_{2j}$ is a valence bond or alkylene of one to 9 carbon atoms, inclusive, with one to 6 carbon atoms, inclusive between $-CR_5R_6-$ and the phenyl ring; wherein T is alkyl of one to 4 carbon atoms, inclusive, fluoro, chloro, trifluoromethyl, or $-OR_7-$ wherein $R_7$ is alkyl of one to 4 carbon atoms, inclusive, and s is zero, one, 2, or 3, with the proviso that not more than two T's are other than alkyl and when s is 2 or 3 the T's are either the same or different; or

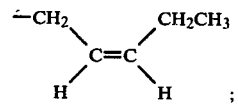  (3)

wherein $R_{30}$ is
$-CH_2OH$
wherein X' is cis$-CH=CH-$, $-C\equiv C-$, or $-CH_2CH_2-$; and wherein $\sim$ indicates attachment in alpha or beta configuration; including the lower alkanoates thereof.

17. A compound according to claim 16 wherein X' is cis$-CH=CH-$.

18. A compound according to claim 16 wherein X' is $-C\equiv C-$.

19. A compound according to claim 18 wherein $Q_3$ is

wherein $R_3$ is as defined in claim 16.

20. A compound according to claim 19 wherein $\text{\textcircled{R}}_{23}$ is

21. A compound according to claim 18 wherein $Q_3$ is

wherein $R_3$ is as defined in claim 16.

22. A compound according to claim 21 wherein $R_{23}$ is

23. A compound according to claim 16 wherein $X'$ is $-CH_2CH_2-$.

24. A compound according to claim 23 wherein $Q_3$ is

wherein $R_3$ is defined as in claim 16.

25. A compound according to claim 24 wherein $R_{23}$ is

26. A compound according to claim 25 wherein L is $-(CH_2)_d-$ wherein d is one to 5, inclusive.

27. A compound according to claim 25 wherein L is $-(CH_2)_t-CF_2$ wherein t is 2, 3, or 4.

28. A compound according to claim 25 wherein L is $-CH_2-CH=CH-A-$ wherein A is a valence bond or $-(CH_2)_h-$ wherein h is one, 2, or 3.

* * * * *

UNITED STATES PATENT OFFICE
CERTIFICATE OF CORRECTION

Patent No. 4,187,224  Dated 5 February 1980

Inventor(s) Udo F. Axen

It is certified that error appears in the above-identified patent and that said Letters Patent are hereby corrected as shown below:

The title should read -- PROSTACYCLIN ANALOGS --.
In the Abstract, that portion of the formula reading

  should read  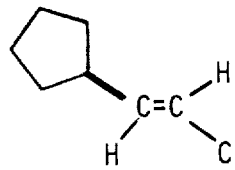

Column 15, line 39, "claim 29" should read -- claim 7 --;
Column 17, line 8, "claim 35" should read -- claim 11 --; line 24, "-CH₂CH=CH-A-" should read -- -CH₂-CH=CH-A- --;
Column 18, line 42, "-C≡-" should read -- -C≡C- --

Signed and Sealed this

Twenty-third Day of December 1980

[SEAL]

Attest:

SIDNEY A. DIAMOND

Attesting Officer  Commissioner of Patents and Trademarks